(12) United States Patent
Timmis et al.

(10) Patent No.: US 8,413,527 B2
(45) Date of Patent: Apr. 9, 2013

(54) FLUID SAMPLING DEVICE

(75) Inventors: Roger James Timmis, Lancashire (GB); Kevin Christopher Jones, Lancaster (GB)

(73) Assignee: Lancaster University Business Enterprises Ltd., Lancaster (GB)

(*) Notice: Subject to any disclaimer, the term of this patent is extended or adjusted under 35 U.S.C. 154(b) by 0 days.

(21) Appl. No.: 12/440,286

(22) PCT Filed: Sep. 13, 2007

(86) PCT No.: PCT/GB2007/050537
§ 371 (c)(1),
(2), (4) Date: Aug. 6, 2009

(87) PCT Pub. No.: WO2008/032116
PCT Pub. Date: Mar. 20, 2008

(65) Prior Publication Data
US 2009/0308181 A1 Dec. 17, 2009

(30) Foreign Application Priority Data
Sep. 13, 2006 (GB) .................................. 0618000.4

(51) Int. Cl.
*G01N 1/20* (2006.01)
(52) U.S. Cl.
USPC ..................................................... 73/863.02

(58) Field of Classification Search .................. None
See application file for complete search history.

(56) References Cited

U.S. PATENT DOCUMENTS

| | | | |
|---|---|---|---|
| 1,964,270 A * | 6/1934 | Nidever et al. | 73/863.02 |
| 2,699,679 A | 1/1955 | Munger | |
| 3,252,323 A | 5/1966 | Torgeson | |
| 3,587,323 A | 6/1971 | Benjaminson et al. | |
| 3,645,694 A * | 2/1972 | Flatau | 436/104 |
| 3,681,973 A | 8/1972 | Ludwig | |
| 4,199,974 A | 4/1980 | Fryberger et al. | |
| 5,085,085 A * | 2/1992 | Anderson | 73/863.02 |
| 5,408,892 A * | 4/1995 | Kawanami et al. | 73/864.33 |
| 7,111,521 B1* | 9/2006 | Andrews, Jr. | 73/863.41 |
| 7,305,895 B1* | 12/2007 | Andrews et al. | 73/863.51 |

FOREIGN PATENT DOCUMENTS

| | | |
|---|---|---|
| EP | 1225436 | 7/2002 |
| WO | 0210712 | 2/2002 |

* cited by examiner

*Primary Examiner* — Robert R Raevis
(74) *Attorney, Agent, or Firm* — Trego, Hines & Ladenheim, PLLC

(57) ABSTRACT

Disclosed is a fluid sampling device comprising a housing arranged to be freely rotatable under the influence of a fluid and comprising an opening for channeling the fluid through the housing such that the fluid contacts a particular portion of a sampling medium corresponding to a relative angular position of the housing.

10 Claims, 8 Drawing Sheets

FLUID SAMPLING DEVICE

The present invention relates to fluid sampling devices and more particularly, but not exclusively, to fluid sampling devices able to provide directional information and requiring no power source.

It is desirable when performing environmental monitoring studies to sample a fluid, typically air or water, and later to analyse the sampled fluid for the presence of one or more substances, including without limitation pollutants.

Typical locations where pollutants may be monitored include: in the vicinity of fossil fuel burning power stations; chemical factories; landfills; major roads; or rivers and estuaries, where there is a risk of contamination from a factory or farm.

There is no limit on the range of different pollutants which can cause environmental problems. In problem situations, or even just as a routine measure, it is normal to sample air- or water-borne pollutants to ensure that safe levels are not exceeded, and to gather evidence for possible enforcement action.

Air-borne pollutants can include gaseous compounds or airborne particulate material (aerosols). Similarly, water-borne pollutants may include soluble compounds, insoluble compounds or larger particulate material.

Current devices tend to be either very simple, such as diffusion tubes which have no directional resolution and may be simply affixed to a suitable surface in the vicinity of where samples are needed, or very complex, such as sampling devices housed in temporary buildings, requiring power sources and vandal-protection equipment. Moreover, these complex devices require site visits by specialist field personnel for purposes of instrument calibration and maintenance.

A problem with the simpler device is that the data it is able to yield only provide an indication that a particular pollutant was present in the vicinity of the sampler at some time during its deployment and does not identify the direction from which it came. However, such devices have the advantage that they are very cheap and easy to deploy and can therefore be used in large numbers in order to provide data from a wide area.

A problem with the more complex device is that it is comparatively expensive, bulky, and requires a suitable vacant site which may have implications for planning permission etc. Moreover, any vacant site that is available may not be where monitoring is most required. e.g. down (prevailing) wind of an industrial installation. It may also be intrusive and prone to tampering and/or vandalism. If it is necessary to sample from several locations, it may not be possible to site enough of the devices to ensure adequate coverage. However, such a device is able to offer more comprehensive data, including the time that particular samples are taken, together with the direction from which the prevailing wind was blowing at that time.

In situations where it is desirable to provide several sampling devices in such a way that directional data may be analysed with a view to locating the source of a particular pollutant, it is not generally possible to do this with current sampling devices. The use of several simple non-directional devices does not provide the required directional sensitivity and the use of several of the more complex devices is not generally practicable, due to cost considerations and to the difficulty of finding enough secure and power-supplied sites for locating such complex devices.

Embodiments of the present invention aim to address these and other problems with the prior art, whether mentioned herein or not.

According to a first aspect of the present invention, there is provided a fluid sampling device comprising a housing arranged to be freely rotatable under the influence of a fluid and comprising an opening for channeling the fluid through the housing such that the fluid contacts a particular portion of a sampling medium corresponding to a relative angular position of the housing.

Suitably, the sampling medium comprises an annulus of material or consists of a plurality of discrete sampling cartridges.

Preferably, the sampling medium is arranged so that a substantial part of the fluid flows through the sampling medium. Alternatively, the fluid flow can be arrange to pass over or otherwise impinge upon a suitable surface of the sampling medium.

Preferably, the housing comprises a tail portion for guiding a fluid inlet towards the prevailing fluid direction.

Preferably, the housing comprises a flow path arranged such that only a defined portion of the sampling medium is exposed to the fluid at any particular time.

Preferably, the flow path is arranged to include a crest so that the fluid rises above the crest and then flows down towards the sampling medium.

Preferably, the sampling medium is arranged to be sensitive to one or more predefined compounds.

Preferably, the sampling medium is impregnated or coated with a marker material whose depuration provides an indication of the volume of fluid which has passed through the medium.

Preferably, the housing is arranged to rotate relative to a frame incorporating the sampling medium by use of slip bearings or contacts.

Preferably, the sampler is arranged to be sensitive to a fluid flow rate whereby the flow path is movable in response to said flow rate.

Preferably, the flow path is movable in response to the flow rate by means of a plurality of cups (e.g. like those of an anemometer in the case of air) which cause the flow path to move in response to changes in fluid flow rate.

Other preferred features of the invention will be apparent from the description and Figures which follow.

For a better understanding of the invention, and to show how embodiments of the same may be carried into effect, reference will now be made, by way of example, to the accompanying diagrammatic drawings in which.

Figure 1:
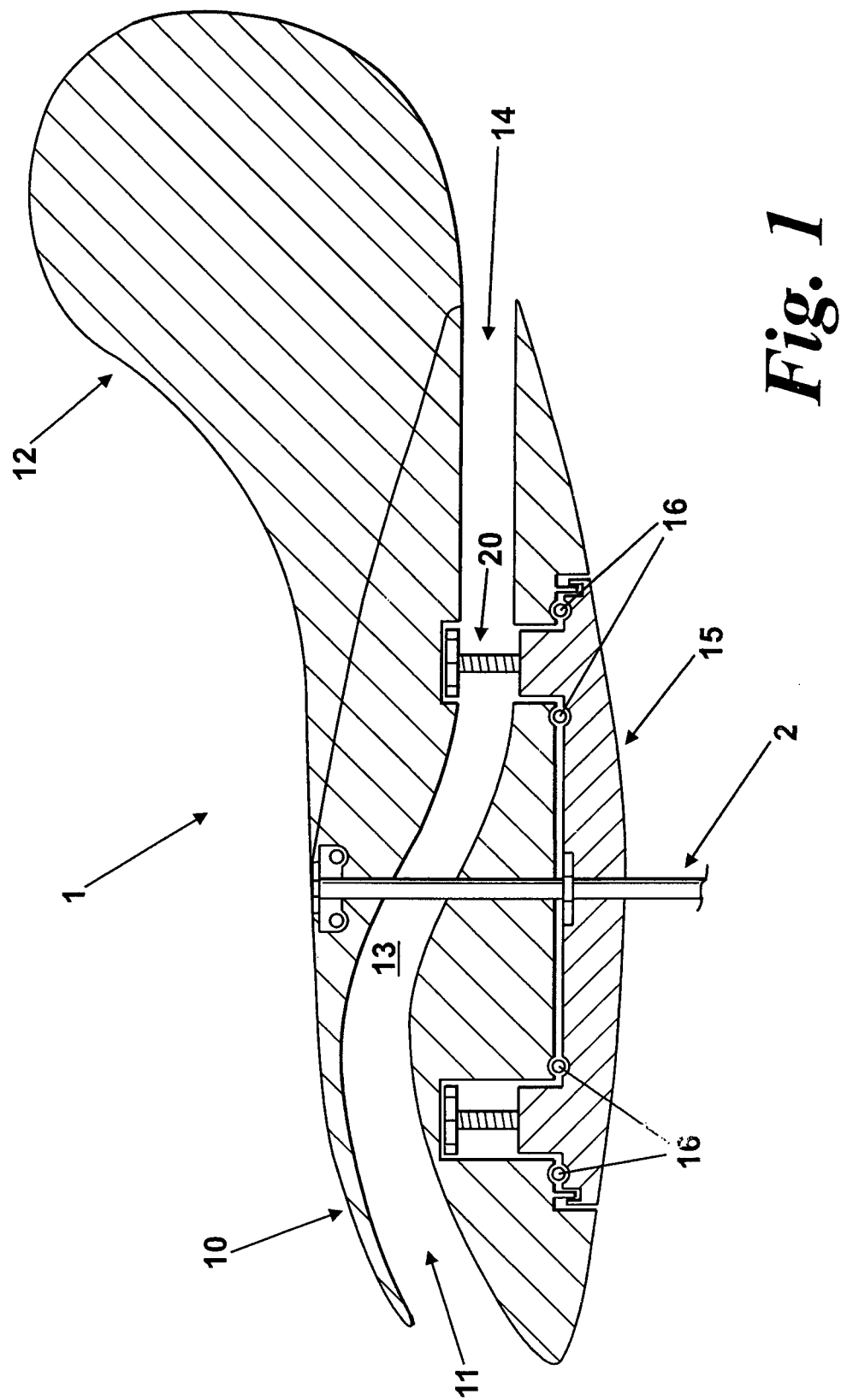
FIG. 1 shows a cross-sectional side view of a fluid sampler according to an embodiment of the invention.

In the following description, the embodiment of the invention will be described with reference to a sampler for use with sampling air. The reader will understand that the sampler can be used equally effectively in a liquid-sampling environment. The mode of operation is essentially identical.

The sampler 1 is arranged to sit atop a suitable pole 2 or other structure so that it is able to receive airflow from a full 360°. Advantageously, since the sampler is a relatively small, temporary structure, planning permission will generally not be required.

The sampler 1 comprises an outer fairing 10, which is arranged to be rotatable so that an opening 11 points into the wind. The rotation of the fairing is achieved by means of a tail 12, which extends from the fairing 11 and causes the sampler to align with the presently prevailing wind. In this way, as the wind direction changes, the opening 11 in the fairing is continuously orientated to point into the wind.

The opening 11 is the entry point to the sampler, by which air to be sampled is delivered to the sampling medium 20. The sampling medium 20 may be configured so that it is sensitive to one or more particular pollutants. Particular arrangements of sampling media will be described later.

In the cross-sectional view, the airway 13 is clearly visible, extending from the opening 11 to the exhaust 14. The airway 13 is arranged such that incoming air is channeled and rises above a crest before passing towards the rear of the sampler, where the sampling medium is located. Immediately after passing through the sampling medium, the air is exhausted through exit 14. The crest is provided at a point higher than the lower point of the upper part of the opening 11 to prevent the ingress of rain or other precipitation.

The sampler is mounted in such a way that the fairing and associated parts, which form the airway, are able to rotate freely under the influence of the wind. The sampling medium 20 is fixed in relation to the pole or other platform to which the sampler is mounted. In this way, air from the prevailing wind direction is passed only to a particular section of the sampling medium 20.

The sampling medium is housed in a detachable frame 15, which is fixed in position relative to the rotating fairing 10. In the embodiments shown in FIGS. 1-5, the frame 15 is arranged to receive a plurality of discrete cartridges or substrate segments, the number of cartridges determining the directional sensitivity of the sampler. In an alternative embodiment, the sampling medium may be provided in the form of a continuous ring or annulus, which is able to provide a greater degree of directional sensitivity.

In either case, the detachable frame 15 is held fixed in position while the fairing 10, which sits atop it on one or more bearings 16, is free to rotate under the influence of the wind.

The sampling medium 20 may take the form of a matrix of material which is coated or impregnated with one or more particular materials which are sensitive to one or more suspected pollutants. The selected material may somehow trap or react with the pollutants. The sampling medium may take the form of inert material, or an impregnated (e.g. with a pollutant-absorbing coating) or reactive material which is porous (e.g. foam), so that it not only traps relevant pollutants, but also allows the main flow of air to pass through it. The sampling medium will be chosen for the pollutants of interest and may embody different forms of construction, different porosities, different densities, different reactivities and different storage capacities.

The sampling medium 20 may be provided in laminate form, with different layers being provided to sample different pollutants.

In the case of a foam material being used, the entire medium may be encased in a fine wire cage to provide structural integrity.

Further details of the sampling medium follow later.

In order to ensure that only a particular section of the sampling medium 20 is ventilated by the incoming airstream, particular attention is paid to ensure that the surrounding parts of the sampling medium are well isolated to avoid contamination of areas immediately adjacent to the area of the medium intended to be ventilated.

It is important when constructing a sampler according to an embodiment of the invention that a defined portion of the sampling medium 20 is ventilated at any given time, so that this portion can be clearly associated with the prevailing flow (e.g. direction, speed). Moreover, the construction should ensure that, as far as possible, only the portion of the sampling medium being so ventilated by the incoming airstream is exposed to the incoming air stream. All other parts of the sampling medium should, as far as possible, be isolated or sequestered, from the airstream so that erroneous results may be avoided or at least minimised.

To achieve the desired degree of isolation, the areas of the sampling medium not being currently ventilated may be separated from the main airflow by a number of measures, designed to ensure minimal unconduited airflow (e.g. close tolerances, bead and groove slip-bearings 16, rotating baffles, contact rollers, segmented enclosures).

Figure 2:
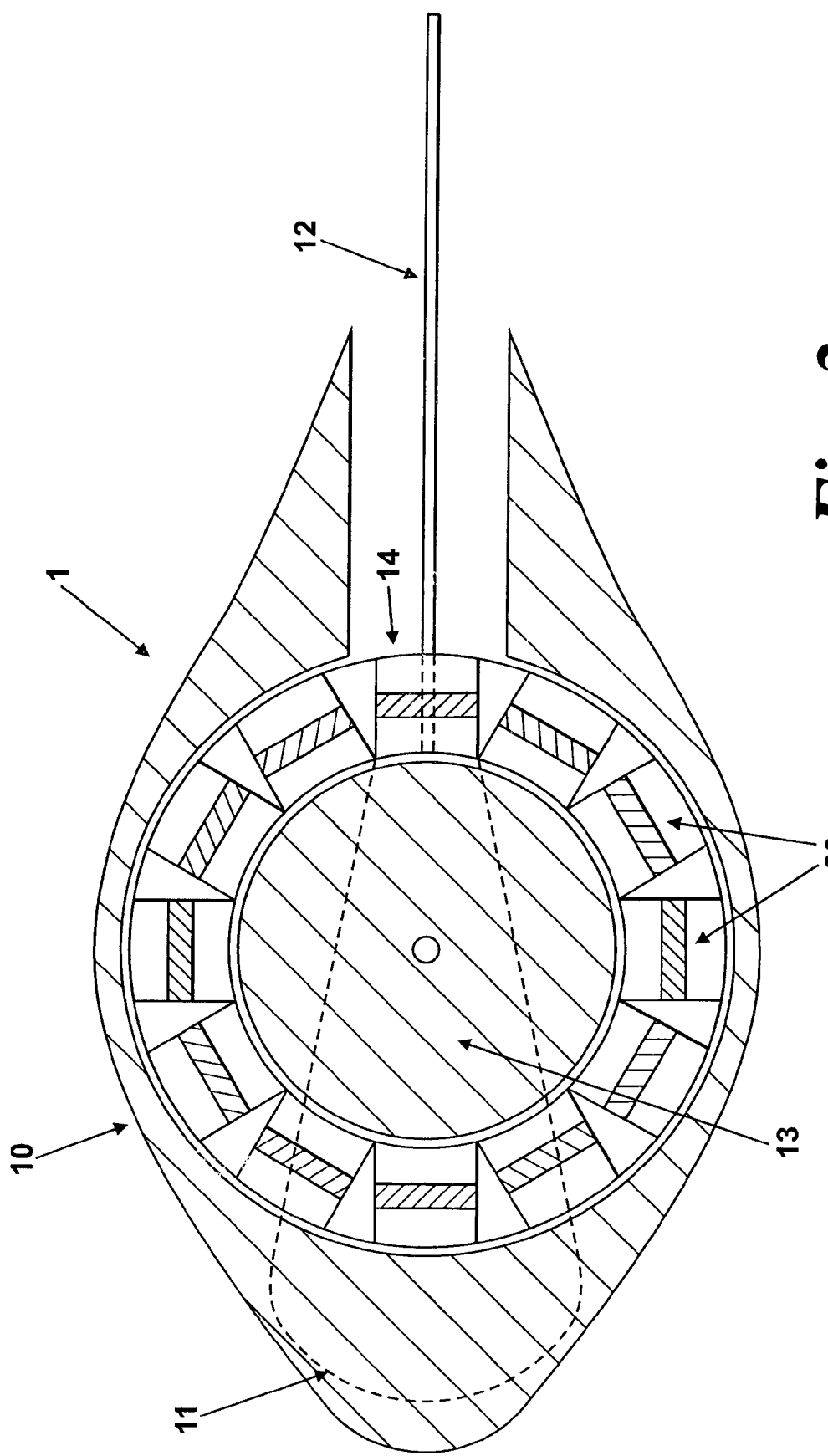
FIG. 2 shows a cross-sectional plan view of a fluid sampler according to an embodiment of the invention.
Figure 3:
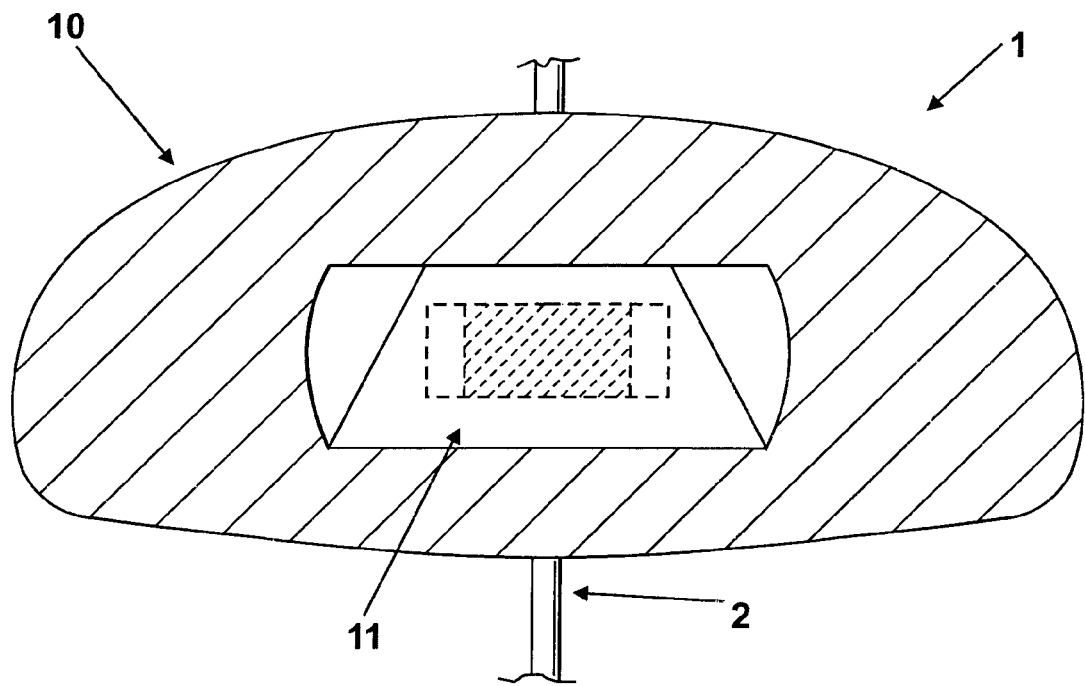
FIG. 3 shows a front view of a fluid sampler according to an embodiment of the invention.
Figure 4:
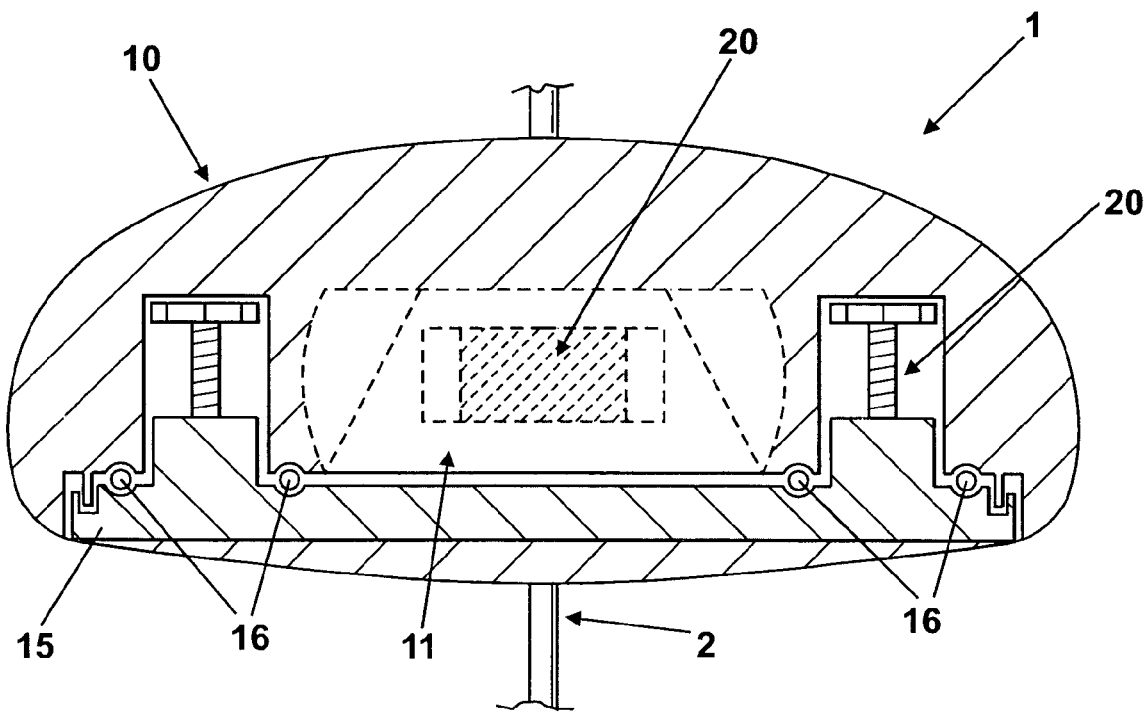
FIG. 4 shows a cross-sectional front view of a fluid sampler according to an embodiment of the invention.
Figure 5:
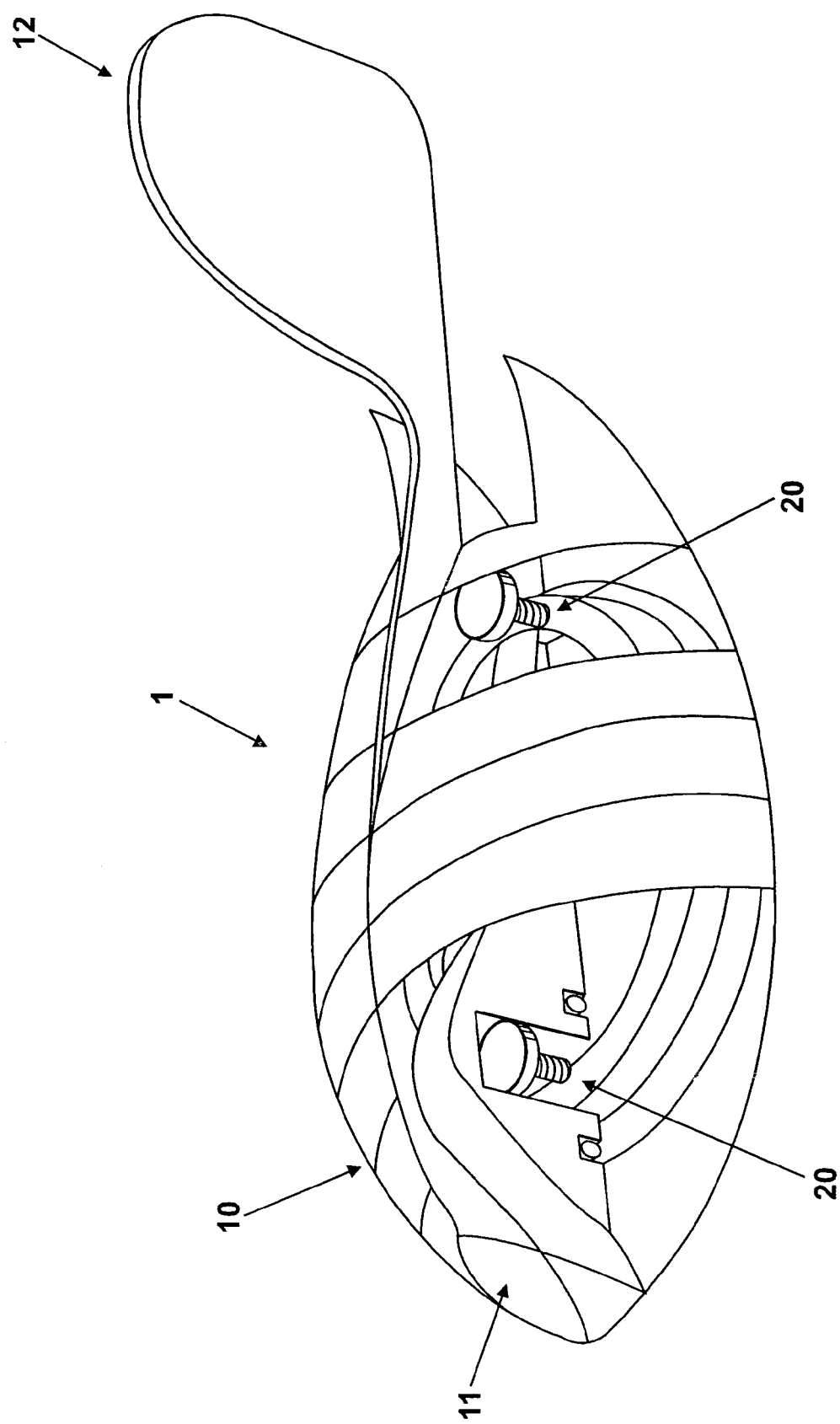
FIG. 5 shows a 3-d partially cut away perspective view of a fluid sampler according to an embodiment of the invention.

As shown in FIG. 2, the airway 13, indicated by the dashed line, shows that only a small section of the sampling medium or, in this case, only one of the twelve sampling cartridges is exposed to the airway 13. The remaining parts of the sampling medium, or the other cartridges, are sheltered.

To further prevent undesired exposure to the airflow, the end of the airway which abuts the sampling medium may be provided with elongate rollers such that the airway channel is in physical contact with the surface of the sampling medium or with the abutting fine wire cage, and the rollers act to minimise airflow around the peripheral edges of the airway. The rollers themselves facilitate easy rotation of the fairing 10.

In an alternative embodiment of the present invention, additional functionality is provided which allows the sampler device to be sensitive to both wind direction and speed. This extra measurable variable enables pollutants to be associated more precisely to particular sources and weather conditions.

Figure 6:
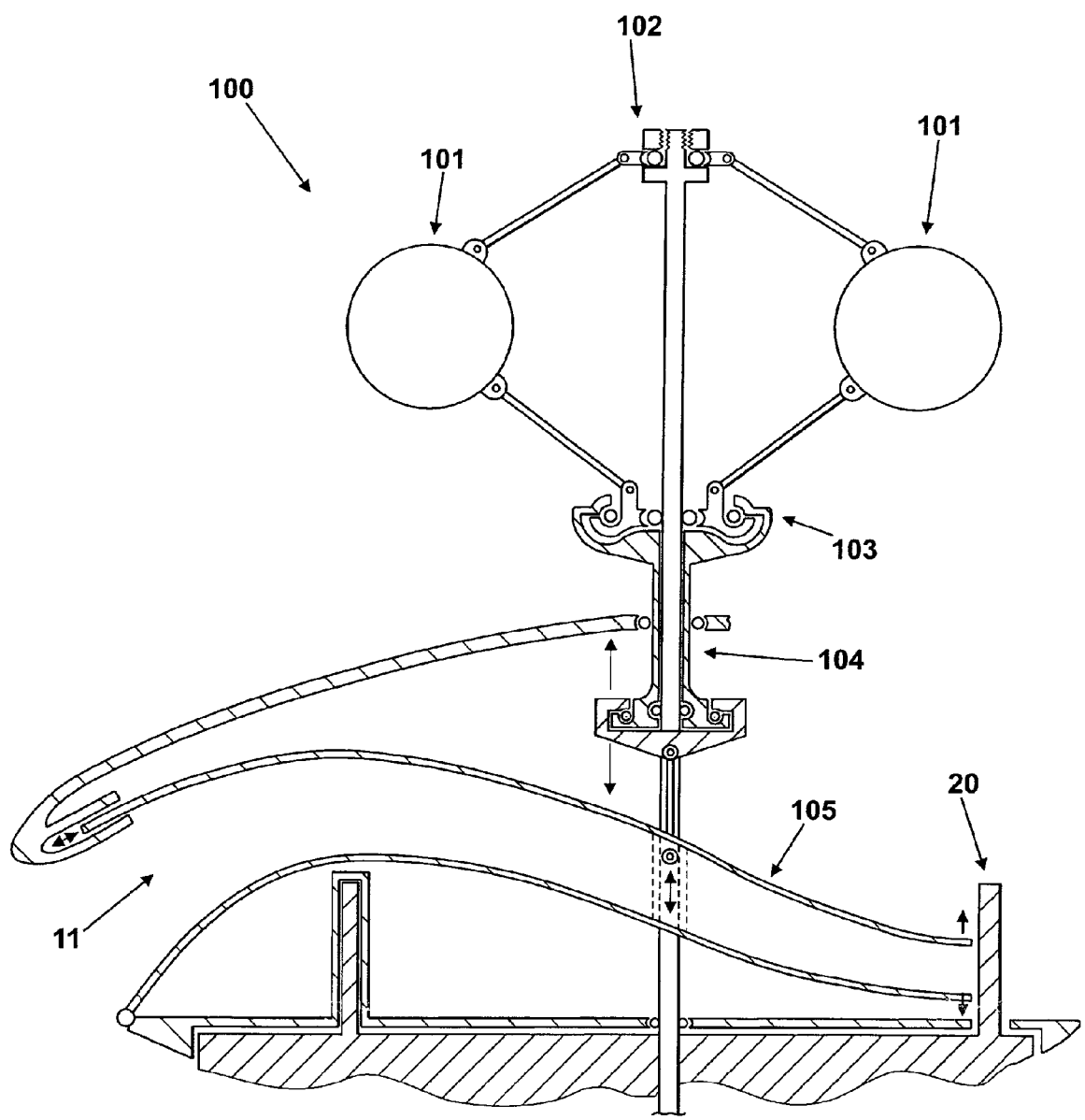
FIG. 6 shows a cross-section of a sampler according to an embodiment of the invention, which is sensitive to windspeed.

FIG. 6 shows an embodiment of the invention which has been adapted so that the airflow is re-directed, internal to the sampler 100, depending on the current windspeed. The particular embodiment shown in FIG. 6 uses a pair of anemometer cups 101 mounted atop the sampler, to provide a governor function.

In use, the sampler 100 rotates into the wind by the action of a tail (not shown), as described previously. However, this embodiment differs to the previous one in that the airflow through the sampler, i.e. from the mouth 11 to the exhaust and passing through the sampling medium 20, is movable vertically. The vertical movement is controlled by the governor formed from the anemometer cups 101.

The anemometer cups 101 are attached in the customary way to an upper collar 102, whose vertical position is fixed, but about which they can rotate. They are also fixed to a movable lower collar 103, which is able to move freely in the vertical direction. The lower collar is attached via a linking member 104 to the airway 105.

At low wind speeds, the anemometer cups 101 will rotate relatively slowly and the lower collar 103 is at the lower end of its range of travel. As such, at lower windspeeds, the lower portions of the sampling medium 20 are ventilated.

At higher windspeeds, the anemometer cups 101 rotate more quickly and, due to centrifugal force, are prone to move away from the central axis about which they rotate. When this happens, the lower collar 103 is forced vertically upwards, which has the effect of moving the airway 105 upwards too. As such, at higher windspeeds, the upper portions of the sampling medium 20 are ventilated.

This mechanism (and similar mechanisms as described below) has the effect of allocating air pollutants systematically to different portions of the sampling medium, in line with different wind speeds. This allocation has the benefit that each portion is less likely to be saturated with accumulated pollution, and is more likely to provide samples that are within the range that can be accommodated by the medium i.e. are within the effective range of measurement.

The airflow path 105 may be constructed in the form of a tube or pipe, leading from the mouth of the sampler to the sampling medium.

Figure 7:
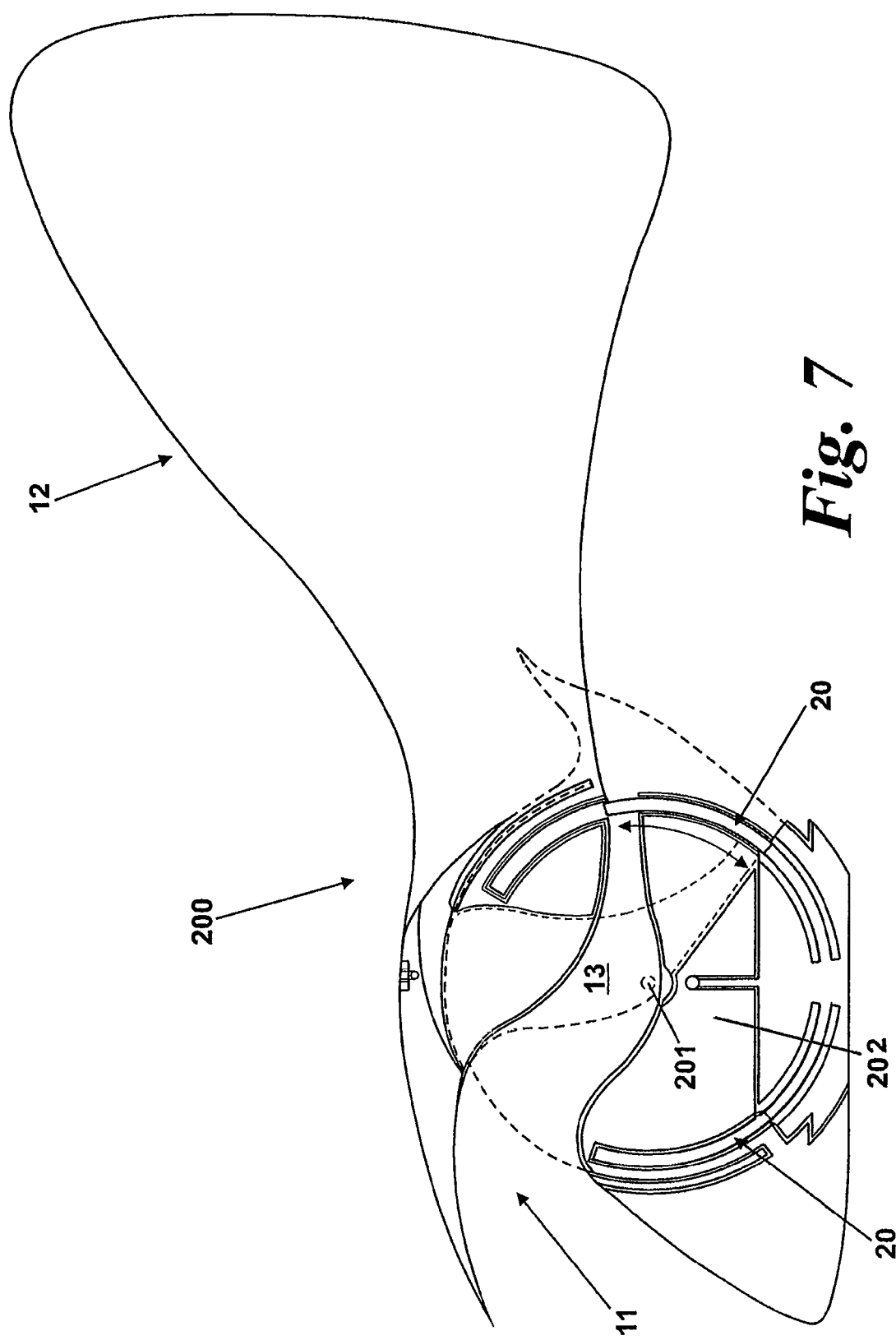
FIG. 7 shows a cross-section of a sampler according to an alternative embodiment of the invention, which is sensitive to windspeed.

FIG. 7 shows an alternative embodiment 200 which is adapted to provide windspeed data. In this embodiment, the airflow path 13 is formed from a member which as well as rotating about a vertical axis with the fairing, is able to pivot about a horizontal axis 201, such that the exit of the airflow path from the pivoting section, where it contacts the sampling medium 20, is able to move up and down the surface of the sampling medium to selectively ventilate portions of the medium.

At low windspeeds, the airflow path is as shown in the solid lined version of FIG. 7. Air entering the mouth 11 of the sampler is directed along the airflow 13 and exits the pivoting part at an upper portion of the sampling medium.

At higher windspeeds, air entering the mouth 11 of the sampler causes the pivoting airflow path to rotate about the horizontal axis 210 due to the pressure of the air exerted on the roof of the airflow path. The airflow is then channeled along the now pivoted airway to a lower portion of the sampling medium 20. A counterweight 202 is fitted centrally under the floor of the pivoting airflow path so that, during pivoting, the moment of the counterweight around the horizontal axis acts progressively to oppose the moment due to the pressure of the air on the roof of the airflow path.

The sampling medium in this embodiment has an arcuate inner surface to conform to the path traced by the exit of the pivoting airflow part.

The particular configuration of the pivoting part allows for a degree of self-limiting in stronger wind conditions. As the airflow increases, the area of the mouth 11 of the pivoting part is decreased as pivoting occurs. Also a rotating baffle intervenes progressively to reduce the effective inlet aperture. Moreover, as the wind strengthens, an increasing proportion of the airflow is diverted around the top of the pivoting part and exhausted from the rear of the sampler. This can prevent the sampling medium from becoming saturated or overwhelmed in high wind conditions.

The downwind end of the sampler in FIG. 7 incorporates a flare which causes the airflow to diverge—so creating a low-pressure zone which helps to pull air through the sample matrix 20. The size of the flare is progressively tapered around the arcuate outlet so that low wind speeds are assisted through the matrix more than high wind speeds. This helps to improve sampling at low windspeeds, but to avoid saturation at high wind speeds.

The pivoting part is carefully weighted so that it is generally biased to the position shown in the solid line in FIG. 7.

In a further alternative embodiment, it is possible to configure the apparatus according to an embodiment of the invention such that it is not necessary for the fluid being sampled to pass through the sampling medium. Instead, the fluid flow path can be configured such that the fluid to be sampled passes over a surface of a sampling medium such that the surface of the sampling medium is substantially parallel to the fluid flow. This is in contrast to the embodiment described previously whereby a surface of the sampling medium is substantially perpendicular to the fluid flow path.

In a further alternative embodiment, which is a variant of the embodiment just described, a surface of the sampling medium may be physically separated somewhat from the fluid flow path by a plurality of vertical channels positioned atop the sampling medium. In this way, fluid flowing above the vertical channels creates turbulence in the channels, thereby controlling the amount of fluid reaching the surface of the sampling medium. The vertical channels may comprise a honeycomb type lattice disposed across the entire surface of the sampling medium so that turbulent fluid must travel down each of the channels before contacting the sampling medium. Such an arrangement may be beneficial to ensure that the loading of pollutants on the sample medium remains satisfactorily within a designed range bounded by a (lower) limit of detection and by an (upper) limit of saturation.

Figure 8:
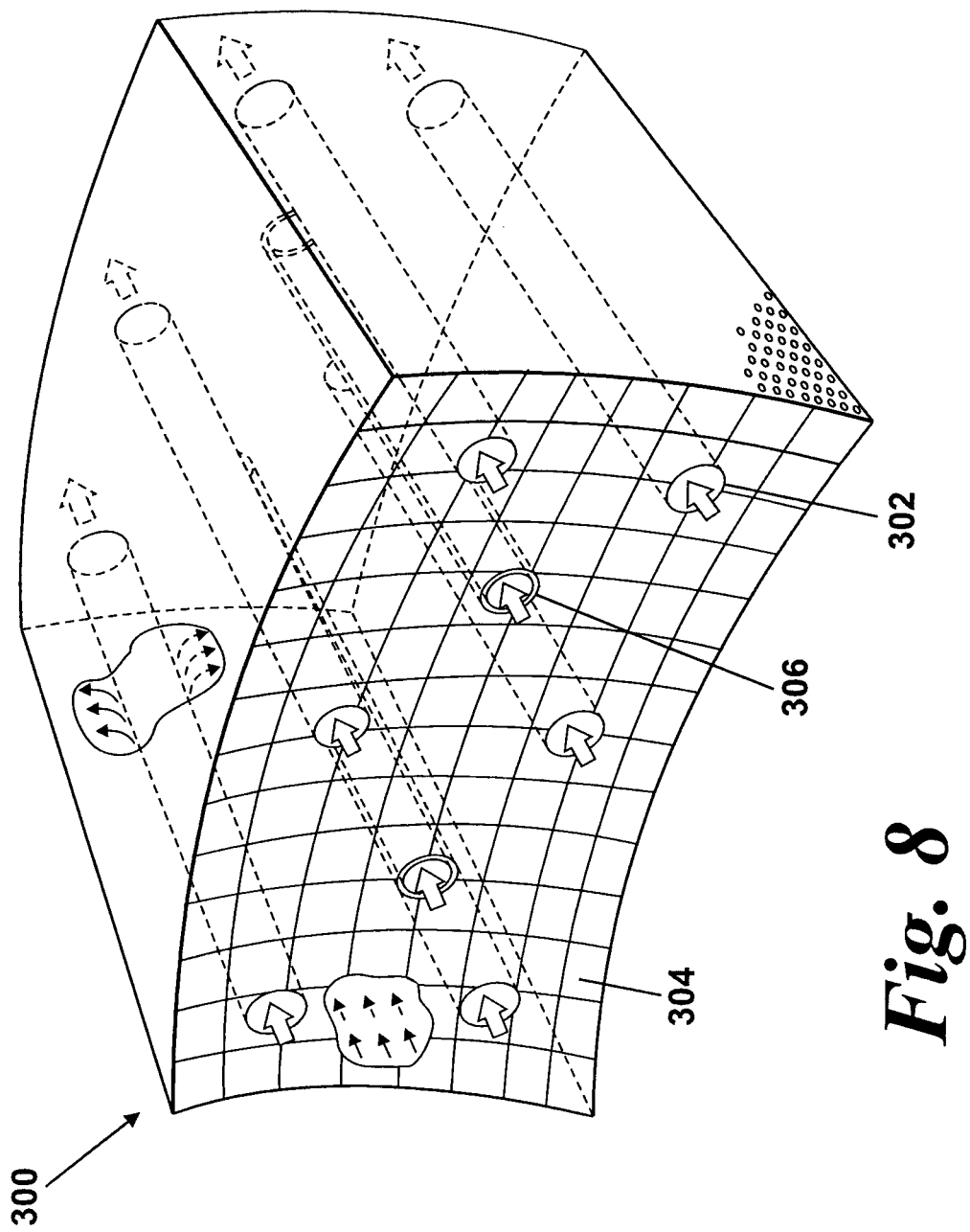
FIG. 8 shows a sampling medium according to an embodiment of the invention.

The sampling medium can take a number of different shapes, depending on the exact configuration of the sampler apparatus. The medium can be composed of one or more materials such as foams, filters, fibres, gauzes or wires and these can be made up as a block, a mesh or multiple layers and can have various pollutant-absorbing coatings. FIG. 8 shows a suitable exemplary medium 300 composed of foam. The medium should demonstrate aerodynamic porosity i.e. it should be sufficiently porous for an airflow to be maintained from the upwind to the downwind side. In the case of a foam block 300, this is achieved by having a number of channels 302, or dynamic airways, whose openings occupy a fraction of the frontal area of the block 300 and provide direct passages for air from front to back. The required amount of aerodynamic porosity is achieved by varying the number, spacing, cross-sectional area, shape and length of these dynamic airways 302.

In general, airborne trace substances must cross through the aerodynamic boundary layer at the surface of the sampling medium 300 in order to be retained in it. The crossing rate depends on the thickness of the boundary layer, which depends in turn on the airspeed above the surface. Low airspeeds generate thicker boundary layers which reduce the rate of crossing/retention, whereas high airspeeds cause boundary layers to thin which increases the rate of crossing/retention. The airspeed near the surface of the medium can be managed by increasing or decreasing the number and width (cross-sectional area) of the dynamic airways 302. For samplers which channel winds of higher and lower speed onto different parts of the medium 300, the boundary-layer thickness can be managed by having wider airways for the parts receiving low-speed flows and narrower airways for the parts receiving higher-speed flows. The design factors to be considered for boundary-layer thickness are closely related to those for aerodynamic porosity, so that the two sets of factors must be considered together.

Another factor to be considered is cellular permeability. This relates to the main body of the sampling matrix 300, away from the dynamic airways 302, which needs to admit air more slowly into a permeable and fine-grained matrix where trace substances can be trapped for later analysis. In the case of a foam block for example, this is achieved by varying the number and size of voids within the foam and the connectivity between them; in practice this means selecting foam with an appropriate density, cell-size, and degree of closure/openness between cells.

The sampling medium 300 needs to be sufficiently rigid to retain its shape under a range of airflows, and not to be distorted under high-flow conditions. In the case of a foam block for example, this is achieved by selecting an appropriate stiffness of foam material or by enclosing a weaker material in a porous wire frame 304 to maintain its shape.

Sampling efficiency refers to the percentage of the mass of a trace substance in the inlet air which is retained in the sampling medium (for later analysis); conversely it relates to the percentage of the inlet mass which transits the sampler without being retained. In general, samplers according to an embodiment of the invention are not designed to intercept and retain 100% of the inlet mass of a substance, as this would mean that the capacity of the sampler would be reached earlier—so that sampling media 300 would have to be replaced more frequently. Instead, samplers according to an embodiment of the invention are designed to retain a small but known fraction of the inlet mass, from which the total flux can be inferred via calibrations. The required design feature is therefore a low sampling efficiency which is consistent or varies systematically with wind speed, and which can be readily determined from calibrations.

The sampling medium 300 is preferably configured to have a high sampling capacity. Sampling capacity relates to the maximum cumulative loading of a trace substance that can be retained on the matrix. Once this capacity has been reached, any further inputs of trace substances will pass through the saturated medium and so will be lost for measurement purposes. Sampling media with low capacities must be replaced more frequently than those with high capacities.

A typical sampling medium comprises a basic substrate or matrix whose outer and inner surfaces are coated with a reactive chemical agent that is designed to retain one or more specific trace substances. It is important that the medium can be easily and evenly coated with the reactive chemical, and that the coating adheres well i.e. that the matrix and coating bind together well. In general, the coating should not block the pores of the sampling medium (or it should only block pores of less than a given size) and it should result in a homogenous surface for chemical reactions. It is therefore desirable that the sampling medium can be easily and evenly "coatable" with reactive agent(s) which bind well to the medium.

The sampling matrix and/or coatings, should be chosen or designed so that they do not degrade in storage or during exposure to ambient conditions in the field. Furthermore, the medium should be configured to have an even homogeneity i.e. different portions of a foam matrix should have the same density and pore size.

The sampling medium 300 is further provided with depuration channels 306, which include discrete tubes with airtight walls but open ends and whose inner surfaces have been coated with evaporative materials (depurants). These tubes act as additional airways so that during sampling the airflow passing through the tube causes some of the material to evaporate at a rate that depends on the run of wind (i.e. volume of air passing) over the sampling period. These channels are therefore designed for passive "run-of-wind" monitoring, and the information can be used to infer the amounts of airflows containing trace substances. For samplers which channel winds of higher and lower speed onto different parts of the medium, these depuration channels can be used to infer the "runs of wind" at different speeds. The sampling medium should be selected to be suitable for housing depuration channels.

The properties and design features of the matrix 300, set out above, are not fixed, but may be varied and optimised for the specific trace substance(s) being sampled. For example, the optimum for sampling of airborne particulates will differ from that for sampling of trace gases; also different sampling media may be placed in series along the airflow. It should be noted that the performance of the sampling matrix is calibrated for each case in controlled conditions (e.g. in a wind tunnel) so that the quantities of substances trapped can be related systematically to the quantities in the incoming air flow.

Figure 9:
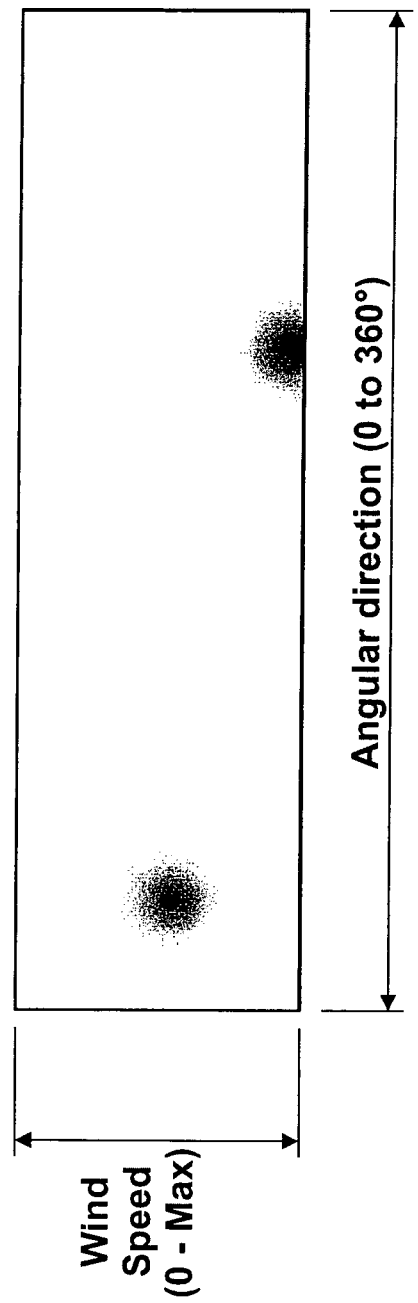
FIG. 9 shows a plot of a typical result of measurements taken from a sampler according to an embodiment of the invention.

FIG. 9 shows a representation of an annular sampling medium which has been opened out into a rectangle to reveal the measure pollutant results. The horizontal axis represents angular direction of arrival (0 to 360°) and the vertical axis represents wind speed from 0 to a predefined maximum value.

The intensity of the developed image at each point indicates the amount of captured substance occurring for the relevant direction and wind speed.

The leftmost result shows a higher concentration of pollutant at a certain angular direction and at a particular windspeed. This demonstrates a characteristic known as 'plume knockdown', whereby a discharge from a chimney or smokestack is not being released at a high enough elevation to be successfully dispersed in the atmosphere and, at certain speeds, a measurable level of pollution is observable. This type of result may reveal design or operational flaws in chemical works, power stations or similar installations. It could also indicate the occurrence of wind-raised air pollution e.g. dusts ablated by the wind from loose surfaces at stockpiles, construction sites or waste-handling facilities.

The rightmost result shows a higher concentration of pollutant at a different angular direction, which tends to decrease as windspeed increases. This type of result is typical of pollution from low-elevation sources, which is progressively dispersed under higher wind speeds. A typical source of such pollution is motor vehicles.

Clearly, the addition of the ability to discriminate between angular directions and also wind speed greatly increases the utility of fluid sampling devices for source attribution purposes.

By installing a plurality of such devices at carefully selected locations, and by monitoring and analyzing the results obtained, it is possible, using techniques such as triangulation, to accurately locate not only the source of a particular pollutant, but also to ascertain under what windspeed conditions the source poses greater problems to the environment.

In a further enhancement of embodiments of the invention, it is possible to infer the volume of air ("run of wind") passing through various parts of the sampling medium. This may be achieved by coating or impregnating the sampling medium with a material which is depurated by passing air.

The marker material, intended to be depurated, may be impregnated into the sampling medium so that it is distributed evenly throughout the medium, or it may be provided as a layer on an outer surface of the sampling medium or located within the medium itself.

As air passes through the ventilated part of the sampling medium, then the marker material is depurated by the passage of air. The amount of depuration is proportional to the amount of air passing. In this way, once the sampling medium is removed and processed, then a plot may be produced which relates angular direction to volume of air. In embodiments equipped to provide windspeed data, then the volume of air may also be plotted against wind speed as well as angular direction.

A suitable marker/depuration chemical will be chosen depending on the analytes of interest, the analytical methods to be employed, the exposure time and the airflow regime.

Embodiments of the present invention therefore offer many advantages over prior art solutions. In particular, they offer the opportunity to collect directional fluid-flow data using only a small passive device, which does not require a power source (either internal or external) or a special housing (e.g. a building in a fenced enclosure, a trailer, a large vandal-proof container), and so opens up many more potential sites for directional pollution monitoring.

The relatively low cost of a device, according to an embodiment of the invention, is likely to mean that several can be deployed at various geographical positions and vertical heights above ground around a suspected site, allowing more data to be generated and leading to a more accurate analysis of the situation. Also, the low cost of the devices makes it practical to deploy them in quantity in situations where some devices may be lost due to vandalism.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A fluid sampling device comprising a housing arranged to be freely rotatable under the influence of a flow of a fluid and comprising an opening configured for channeling a portion of the fluid through the housing such that said portion of the fluid contacts a particular portion of a sampling medium corresponding to a relative angular position of the housing, wherein the sampling medium comprises an annulus of material.

2. A device as claimed in claim 1 wherein the sampling medium is arranged so that a substantial part of the portion of the fluid flows through the sampling medium.

3. A device as claimed in claim 1 wherein said portion of the fluid is arranged to pass over or otherwise impinge upon a suitable surface of the sampling medium.

4. A device as claimed in claim 1 wherein the housing comprises a tail portion for guiding a fluid inlet towards the prevailing fluid direction.

5. A device as claimed in claim 1 wherein a fluid flow path is arranged to include a crest arranged such that said portion of the fluid rises above the crest and then flows down towards the sampling medium.

6. A device as claimed in claim 1 wherein the sampling medium is arranged to be sensitive to one or more predefined compounds.

7. A device as claimed in claim 1 wherein the housing is arranged to rotate relative to a frame incorporating the sampling medium by use of slip bearings or contacts.

8. A fluid sampling device comprising a housing arranged to be freely rotatable under the influence of a flow of a fluid and comprising an opening configured for channeling a portion of the fluid through the housing such that said portion of the fluid contacts a particular portion of a sampling medium corresponding to a relative angular position of the housing, wherein the sampling medium is impregnated or coated with a marker material whose depuration provides an indication of the volume of fluid which has passed through the medium.

9. A fluid sampling device comprising a housing arranged to be freely rotatable under the influence of a flow of a fluid and comprising an opening configured for channeling a portion of the fluid through the housing such that said portion of the fluid contacts a particular portion of a sampling medium corresponding to a relative angular position of the housing wherein a fluid flow path is movable in response to a fluid flow rate by means of a plurality of cups which cause the fluid flow path to move in response to changes in fluid flow rate.

10. A fluid sampling device comprising: a frame carrying a plurality of discrete sampling cartridges arranged in a circular configuration; and a housing coupled to the frame, the housing arranged to be freely rotatable relative to the frame under the influence of a flow of a fluid, the housing comprising an opening communicating with an environment exterior to the fluid sampling device, an exit communicating with the environment exterior to the fluid sampling device, and an airway extending through the housing from the opening to the exit, wherein the airway is configured for: receiving a portion of the fluid from the opening, channeling said portion of the fluid through the housing such that said portion of the fluid contacts a particular one of the sampling cartridges corresponding to a relative angular position of the housing, and exhausting said portion through the exit.

* * * * *